United States Patent [19]
Spivack et al.

[11] Patent Number: 5,049,498
[45] Date of Patent: Sep. 17, 1991

[54] FUNGAL STRAIN USED TO MAKE 2',4,4''-M-TERPHENYLTRIOLS

[75] Inventors: James L. Spivack, Cobeskill; David P. Mobley, Schenectady; David K. Dietrich, Schenectady; Joseph J. Salvo, Schenectady, all of N.Y.

[73] Assignee: General Electric Company, Schenectady, N.Y.

[21] Appl. No.: 632,888

[22] Filed: Dec. 24, 1990

[51] Int. Cl.[5] .............................................. C12R 1/66
[52] U.S. Cl. .................................. 435/156; 435/254; 435/913
[58] Field of Search .................. 435/156, 913, 254

[56] References Cited

U.S. PATENT DOCUMENTS

| | | | |
|---|---|---|---|
| 4,153,509 | 5/1979 | Schwartz | 435/156 |
| 4,431,736 | 2/1984 | Romesser | 435/156 |
| 4,981,793 | 1/1991 | Johnson et al. | 435/156 |

OTHER PUBLICATIONS

Cox et al., "Biotechnol. Biens. 1985", 27, 1395-1402.
Schwartz et al., "Appl. Environ Microbiol.", Apr. 1980, p. 7028, vol. 39, No. 4.

Primary Examiner—Herbert J. Lilling
Attorney, Agent, or Firm—William H. Pittman; James C. Davis, Jr.

[57] ABSTRACT

*A. parasiticus* is employed to hydroxylate 2'-hydroxyterphenyl compounds to terphenyltriols, which can be used to form branched polycarbonates. The hydroxylation reaction is enhanced by maintaining a sufficient amount of a carbon source in the culture medium-reaction medium to maintain the ammonium level below 300 ppm. during the bioconversion phase. Employment of a mutant strain of *A. parasiticus* which was isolated following ultraviolet light mutagenesis to reduce its tendency to produce aflatoxins is preferred.

4 Claims, No Drawings

FUNGAL STRAIN USED TO MAKE 2',4,4''-M-TERPHENYLTRIOLS

This application is related to earlier filed copending application Ser. No. 07/364,278, filed June 12, 1989, the disclosure of which is hereby incorporated by reference.

This invention concerns the microbiological oxidation of 2'-hydroxy-m-terphenyls to 2',4,4'-m-terphenyltriols. A strain of *Aspergillus parasiticus (A. parasiticus)*, preferably a novel strain with minimal tendency to produce aflatoxins, is employed for the microbiological oxidation. This invention also concerns the slow addition of a carbon source to the culture medium-reaction medium containing such *A. parasiticus* and a biphenyl or terphenyl compound.

Microbiological oxidation of biphenyls by a variety of bacteria and fungi including *A. parasiticus* has been studied. For a discussion of the background of the art see U.S. Pat. Nos. 4,153,509 and 4,431,736, which patents are hereby incorporated by reference, and the references cited therein. *Chemical Abstracts* has a reference to a compound which could be confused with a hydroxylated terphenyl as being disclosed in *J. Chromatogr. Libr.*, 30, 35–44 (1985), but the Chemical Abstracts reference is clearly in error since the publication referred to is directed to phenolformaldehyde condensation products.

A drawback of *A. parasiticus* is its tendency to produce aflatoxins, potent carcinogens and mutagens during the bioconversion reactions leading to the production of hydroxylated aromatic molecules. Some fermentation media, such as those containing corn steep liquor, stimulate aflatoxin production and on a larger scale significant levels of aflatoxins could be produced.

Hydroxylated aromatic molecules have commanded considerable interest in industry due to their many uses in the manufacture of plastics, liquid crystals and dyes. However, some large-scale selective hydroxylations are difficult to carry out by any means.

Often, relatively inexpensive starting materials can be biologically converted to higher value products. One organism capable of performing an interesting bioconversion is *A. parasiticus*. It has been reported that this fungus can transform biphenyl to 4,4'-dihydroxybiphenyl in batch and continuous cultures but the reported rates and concentrations were judged to be too low to be economically attractive. In addition, as stated above, *A. parasiticus* produces carcinogenic secondary metabolites, aflatoxins, which make large-scale fermentations less desirable from a processing standpoint.

In one aspect, this invention is directed to a mutant strain of *A. parasiticus* which does not produce detectable quantities of aflatoxins and is capable of hydroxylating terphenyls in commercial quantities.

In another aspect, the invention is directed to stable aromatic triols with skeletal geometry which imparts useful physical properties to polymers incorporating them. Triols are required to give certain condensation polymers such as polycarbonates a sufficiently branched structure to retain shape in blow molding operations. A fully aromatic triol will confer superior thermal stability as well.

This invention is also directed to the slow addition of a carbon source to the culture medium-reaction medium used to oxidize terphenyl compounds to the corresponding hydroxylated derivatives.

The 2'-hydroxy-m-terphenyl compounds which can be hydroxylated by the process of this invention to produce the m-terphenyltriol compounds are represented by the generic formula

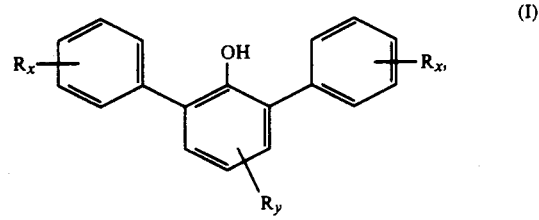

wherein each R is a substituent inert to bioconversion conditions, x has a value from 0 to 4 and y has a value from 0 to 3. Any free position of any ring radical of the 2'-hydroxy-m-terphenyl, except the 4 and 4' position, ma contain an R radical.

Preferred R values are alkyl, alkylamino and alkoxy radicals, especially $C_{1-4}$ alkyl. Preferably, each x and each y is independently 0-2.

The m-terphenyltriols of the present invention are principally 2',4,4'-m-terphenyltriols having the formula

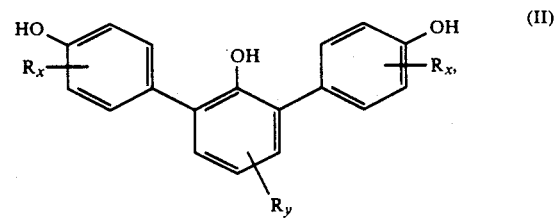

in which R, x and y are as previously defined. A preferred m-terphenyltriol has the formula

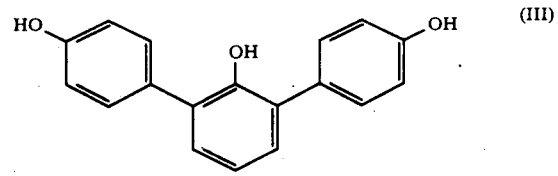

These 2',4,4'-m-terphenyltriols may be prepared by microbiological oxidation of a corresponding 2'-hydroxy-m-terphenyl by the action of *A. parasiticus*. Preferably, the aforementioned strain of *A. parasiticus* which has decreased tendency to produce aflatoxins is employed. Still more preferably, the 2',4,4''-m-terphenyltriol is prepared by the aforementioned slow addition of a carbon source.

The medium in which the *A. parasiticus* is preferably cultivated includes a carbon source, a nitrogen source and deionized water. Suitable carbon sources include glucose, maltose and fructose, with glucose generally being preferred. Readily available forms of glucose such as corn syrup are particularly useful.

As nitrogen sources, such commonly employed materials as ammonium salts, corn steep liquor, peptone, neopeptone, soytone, tryptone and soybean powder may be employed. Corn steep liquor is particularly suitable and is generally preferred.

The culture medium can also contain various trace elements. These are generally conventional in nature, and include boron, copper, zinc, magnesium, iron, manganese and cobalt. They may be furnished in the form of readily available compounds.

The usual method of growing *A. parasiticus* involves a rich medium containing both carbon and nitrogen sources, in which the fungal spores are germinated and grown for about 24 hours. The resulting culture is used to inoculate a larger batch of medium, also for about 24 hours. At the end of this time, near-maximum cell density has been achieved and the available carbon and nitrogen are nearly depleted. This portion of the biochemical process is sometimes hereinafter designated the "growth phase". The compound to be hydroxylated, in the present case the 2'-hydroxy-m-terphenyl, is then added and undergoes oxidation in what is hereinafter termed the "bioconversion phase".

It has been discovered that when all the carbon source and nitrogen source are introduced at the beginning of the growth phase, the ammonium ion concentration of the system increases during the bioconversion phase from a value near zero at the beginning thereof. Concurrently, the pH of the system increases. When the ammonium ion concentration exceeds about 300 ppm., the conversion of 2'-hydroxy-m-terphenyl to triols ceases.

It has further been discovered that the bioconversion phase can be prolonged if carbon source is added gradually during said phase. One effect of such gradual addition is to maintain the ammonium ion concentration at a low level. The rate of pH increase is concomitantly retarded.

It is believed that the effect of gradual addition of carbon source during the bioconversion stage is based on the property of *A. parasiticus* to undergo different metabolic processes in various life stages. Thus, such gradual addition keeps the organism in the metabolic state in which the desired bioconversion takes place, while an increase in ammonium ion concentration is a signal that the organism is leaving this metabolic state. The concentration of ammonium ion in the system can be used as an index of the proper rate of addition of the carbon source. If the rate of addition is too high, the bioconversion stops, most likely because of catabolite repression.

Thus, it is well within the state of the art to regulate the addition rate of the carbon source to obtain optimum results. Both constant and variable addition rates may be employed. Suitable addition rates are often in the range of about 0.001-1.0, preferably about 0.05-0.5 and most preferably about 0.1 gram/liter/hour.

This use of carbon source addition to control the metabolic state of *A. parasiticus* is not only applicable to the hydroxylation of 2'-hydroxy-m-terphenyl compounds but also to the hydroxylation of all biphenyl and terphenyl compounds having a free hydroxylation site. A method employing such addition is disclosed and claimed in copending, commonly owned application Ser. No. 071632,887.

The pH of the culture medium may vary from about 3.5 to about 9 and preferably from about 5.5 to about 7. It is often convenient to buffer the pH in this range by employing as a nitrogen source corn steep liquor, or peptone, which contain buffering amino acids, or by acid or base addition. Cultivation temperatures of the *A. parasiticus* are typically in the range of about 20°-40° C. and preferably about 30°-37° C.

The 2'-hydroxy-m-terphenyl to be oxidized may be introduced into the culture medium neat (i.e., in the absence of solvent) or in a suitable solvent which is non-toxic to the microorganism. Methanol and ethanol are illustrative of such solvents.

In a preferred embodiment of this invention, the substrate is added as a fine aqueous dispersion, allowing for the addition of large amounts of substrate with maximum available surface area for interaction with the microorganism and further avoiding the inhibition of microorganism growth and activity which may occur with even low concentrations of organic solvents. Such dispersions can be easily prepared; for example, by high-shear stirring of the molten substrate at temperature above the melting point thereof with gelatin as an emulsifying agent, followed by cooling to ambient temperature with continued stirring. Using such a technique, substrate particle size can be reduced to less than 10 microns.

Additionally, as an alternative to preparing a fine dispersion of the substrate, such substrate can be admixed or dispersed in a surfactant before addition to the culture medium. Generally such surfactants are useful in amounts in the range of about 0.1-0.6% by weight of the culture medium-reaction mixture.

Examples of suitable surfactants include octylphenylethylene oxide, available as Noniodet P40 and as Triton X-100. The formula of these materials is

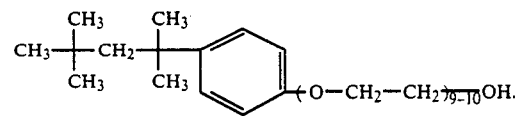

Additional examples of surfactants are polyoxyethylene (20) acetyl ether and polyoxyethylene (4) lauryl ether, available as Brij, 58 and 30, respectively; polyoxyethylene nonylphenyl ether and polyoxyethylene octylphenyl ether, available as Igepal CO and CA, respectively; and polyoxyethylene (20) sorbitan monolaurate, polyoxyethylene (20) monooleate and polyoxyethylene (20) sorbitan monopalmitate, available as Tweens, 20, 80 and 40, respectively. The presence of such surfactants in the culture medium containing microorganism and the reactant/substrate is believed to maximize microorganism-substrate contact by enhancing solubility of the sparsely water-soluble substrate. The presence of a surfactant has been found to substantially increase product concentration.

The concentration of the *A. parasiticus* required to practice the process of this invention is typically about 1-2% by weight (dry), particularly in the case of *A. parasiticus* grown on corn steep liquor.

The mutant strain of *A. parasiticus* of the present invention, which has reduced tendency to produce aflatoxins, has been deposited with the American Type Culture Collection in Rockville, MD, on October 16, 1990, as ATCC 74022. It has been found to give results in the hydroxylation of biphenyl and m-terphenyl compounds including 2'-hydroxy-m-terphenyl which compare favorably to the results obtained using the wild type *A. parasiticus*. For comparative studies see Biosynthesis of p-Hydroxylated Aromatics by Joseph J. Salvo et al., *Biotechnol. Prog.*, 6, 193-197 (1990), the disclosure of which is hereby incorporated by reference.

Aflatoxin minus strains of *A. parasiticus* have been generated in the past by standard UV or chemical mutagenesis techniques. The techniques are described by Bennett, J.W.; Papa, E.D., Genetics of Aflaxtoxigenic Aspergillus Species, in *Advances in Plant Pathology*;

Sidhu, G.S., Ed.; *Genetics of Pathogenic Fungi,* Vol. 6; Academic Press: London, 1988; pp. 263–280, which disclosure is hereby incorporated by reference.

The method of creating a mutant strain of *A. parasiticus* which produces less aflatoxins than an aflatoxin producing wild type of *A. parasiticus* comprises treating the spores of the wild type with ultraviolet light and screening for colonies which produce at least 100-fold less aflatoxins than the wild type *A. parasiticus* grown under identical conditions, screening these colonies for hydroxylation of terphenyl compounds and selecting one or more strains which produce terphenyltriols in high yield. The *A. parasiticus strain of the present invention, isolated by this procedure, produces no detectable aflatoxins (i.e., less than* 20 ppb.) and produces a yield of terphenyltriols at least 90% as great as that obtained using the parent wild type of *A. parasiticus.*

The invention is illustrated by the following examples. All parts and percentages are by weight unless otherwise specified.

EXAMPLE 1

Spores of *A. parasiticus* strain ATCC 15517 were plated on Sabouraud Dextrose (Difco) with Bacto agar added to 1.5%, and irradiated with a germicidal UV light source at 60 microwatt hours per square centimeter measured at the culture plate surface. Approximately 99% of the irradiated spores failed to germinate. Spores that did germinate were transferred to aflatoxin production plates as described by Lennox and Davis, "Selection of and Complementation Analysis Among Aflatoxin Deficient Mutant of *Aspergillus parasiticus*", *Exp. Mvco.,* 8, 192–195 (1983), which description is hereby incorporated by reference. Four colonies were inoculated per plate with a wild-type control at the center. Decreased aflatoxin producers were screened by illuminating the plates with a long-wave UV lamp (366 nm.) and by looking for the absence of a blue halo, which normally surrounds a wild-type colony. Several low-level aflatoxin producers were isolated after screening several thousand colonies that developed from UV-irradiated spores.

Thin layer chromatography and high pressure liquid chromatography were used to detect aflatoxins after extraction from spent media, mycelia or agar plates. Aflatoxin standards (Sigma) were always run in parallel. These analyses showed that strain JS 1-89 produced no detectable aflatoxins. The hydroxylation activity of strain JS 1-89 was comparable to wild type isolates.

EXAMPLE 2

The spore production agar employed in this example was prepared by dissolving in water 218 g. of sorbitol, 5 g. of yeast extract, 20 ml. of Aspergillus minimal salts solution, 1 ml. of trace elements solution, 10 g. of glucose and 15 g. of Bacto-Agar, autoclaving the solution and combining it with 10 ml. of 0.2M magnesium sulfate heptahydrate solution. The Aspergillus minimal salts solution was prepared by dissolving in 1 liter of water 300 g. of sodium nitrate, 75 g. of potassium dihydrogen phosphate and 25 g. of potassium chloride and adjusting the pH to 6.5 by addition of sodium hydroxide. The trace elements solution was prepared by dissolving in 1 liter of water 500 mg. of boric acid, 40 mg. of cupric sulfate pentahydrate, 100 mg. of potassium iodide, 200 mg. of ferric chloride monohydrate, 160 mg. of molybdic acid and 400 mg. of zinc sulfate heptahydrate. The spore harvesting buffer was an aqueous solution of 1% sodium chloride, 0.1% Triton X-100 surfactant and 20% glycerol.

A stock of spores of strain JS 1-89 was prepared by inoculating spore production agar with $5\times10^5$ spores of the strain and incubating for two days at 30.C, then at room temperature until a heavy "lawn" of green spores had developed. They were suspended in spore harvesting buffer, spun down, resuspended in fresh buffer, diluted to the desired concentration and stored at $-80°$ C. An inoculum culture was prepared by charging five 2-liter baffled Erlenmeyer flasks with 400 ml. of sterile Sabouraud Dextrose, inoculating with JS 1-89 spores at $6\times10^8$ spores per flask and incubating for 24 hours at 37° C.

A 400-liter straight-sided polyethylene tank fitted with a motor-driven stirrer was chemically sterilized with sodium hypochlorite and isopropyl alcohol, charged with 300 liters of an aqueous solution comprising 22 g./l. Karo corn syrup, 43 g./l. Argo Steepwater E801 corn steep liquor and 20 mg./l. tetracycline hydrochloride as a bacterial suppressor, inoculated with the contents of the spore germination flasks, and sparged with sterilized air at 37.C for 24 hours. There were then added, with stirring, 600 grams of 2'-hydroxy-m-terphenyl, 1200 grams of Triton X-100 surfactant and 15 grams of 4,4'-biphenol as a promoter. Air sparging was continued as an aqueous solution containing 300 g./l. of corn syrup was added at 0.05 g./l./hr. of corn syrup for the first 65 hours, 0.12 g./l./hr. for the next 95 hours and 0.008 g./l./hr. until bioconversion was complete. The pH and ammonium ion concentration of the mixture were monitored during the bioconversion.

When bioconversion was complete, the mixture was brought to a pH of 12 and the contents were centrifuged. The solids were reslurried at pH 12 and recentrifuged and the combined liquid phases were acidified to a pH of 7 and extracted with ethyl acetate. The extracts were purified by liquid/liquid extraction and flash chromatography to yield 102 grams of 2',4,4'-m-terph structure of the product was confirmed by proton and carbon-13 nuclear magnetic resonance and mass spectrometry and it was shown by high pressure liquid chromatography and gas chromatography to be greater than 99% pure.

What is claimed is:

1. A method for preparing a 2'4,4"-m-terphenyltriol which comprises microbiologically oxidizing a corresponding 2'-hydroxy-m-terphenyl by the action of *A. parasiticus.*

2. The method of claim 1 wherein the 2'-hydroxy-m-terphenyl has the structural formula 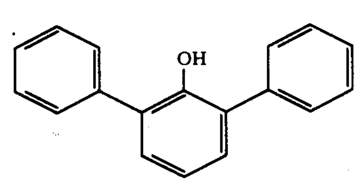 and the terphenyl triol has the structural formula

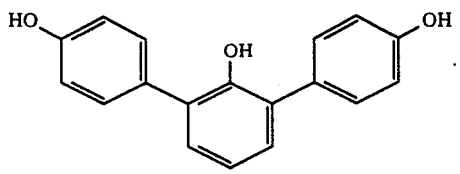

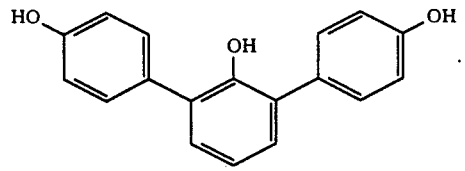

3. The method of claim 1 wherein a nonionic detergent is present in the amount of about 0.1–0.6 by weight of the reaction mixture.

4. The method of claim 1 wherein the *A. parasiticus* has been modified to reduce the production of aflatoxins.

* * * * *

3. The method of claim 1 wherein a nonionic detergent is present in the amount of about 0.1–0.6 by weight of the reaction mixture.

4. The method of claim 1 wherein the *A. parasiticus* has been modified to reduce the production of aflatoxins.

* * * * *

UNITED STATES PATENT AND TRADEMARK OFFICE
CERTIFICATE OF CORRECTION

PATENT NO. : 5,049,498

DATED : September 17, 1991

INVENTOR(S) : James L. Spivack and Joseph J. Salvo

It is certified that error appears in the above-identified patent and that said Letters Patent is hereby corrected as shown below:

ON TITLE PAGE:

Item [75]    the names of David P. Mobley and David K. K. Dietrich as joint inventors should be removed.

Signed and Sealed this

Fourteenth Day of January, 1992

Attest:

HARRY F. MANBECK, JR.

*Attesting Officer*   Commissioner of Patents and Trademarks